United States Patent
Green

(10) Patent No.: US 6,259,806 B1
(45) Date of Patent: Jul. 10, 2001

(54) METHOD AND APPARATUS FOR TRANSFORMING COORDINATE SYSTEMS IN A TELEMANIPULATION SYSTEM

(75) Inventor: Philip S. Green, Redwood City, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 09/174,051

(22) Filed: Oct. 15, 1998

Related U.S. Application Data

(63) Continuation of application No. 08/783,644, filed on Jan. 14, 1997, now Pat. No. 5,859,934, which is a continuation of application No. 08/239,086, filed on May 5, 1994, now Pat. No. 5,631,973, and a continuation-in-part of application No. 08/709,930, filed on Sep. 9, 1996, now Pat. No. 5,808,665, which is a continuation of application No. 08/517,053, filed on Aug. 21, 1995, now abandoned, which is a continuation of application No. 07/823,932, filed on Jan. 21, 1992, now abandoned.

(51) Int. Cl.[7] ..................................... G06K 9/00
(52) U.S. Cl. ..................... 382/128; 382/311; 606/104; 606/109; 606/118
(58) Field of Search .................................. 382/128, 311; 600/101, 103, 104, 109, 114, 118, 160

(56) References Cited

U.S. PATENT DOCUMENTS

| | | | |
|---|---|---|---|
| 4,853,874 | 8/1989 | Iwamoto et al. | 364/513 |
| 5,046,022 | 9/1991 | Conway et al. | 364/513 |
| 5,182,641 | 1/1993 | Diner et al. | 358/103 |

(List continued on next page.)

FOREIGN PATENT DOCUMENTS

| | | | |
|---|---|---|---|
| 0 291 965 | 11/1988 | (EP) | B25J/9/18 |
| 0 323 681 | 7/1989 | (EP) | G05B/19/417 |
| 0 411 498 | 2/1991 | (EP) | G05B/19/405 |
| 2 128 842 | 5/1984 | (GB) | H04N/7/18 |
| WO 93/05479 | 3/1993 | (WO) | G06F/15/46 |
| WO 95/01757 | 1/1995 | (WO) | A61B/19/00 |

OTHER PUBLICATIONS

Bajura et al., "Merging virtual objects with the real world: Seeing ultrasound imagery within the patient" Computer Graphics (Jul. 1992) 26(2):203–210.

Gayed et al., "An advanced control surgical micromanipulator for surgical applications" Systems Science (1987) 13(1–2):123–134.

Hunter et al., "Ophthalmic microsurgical robot and associated virtual environment" Comput. Biol. Med. (1995) 25(2):173–182.

(List continued on next page.)

Primary Examiner—Matthew C. Bella
(74) Attorney, Agent, or Firm—Towsend Townsend & Crew LLP; Mark D. Barrish, Esq.

(57) ABSTRACT

In a telemanipulation system for manipulating objects located in a workspace at a remote worksite by an operator from an operator's station, such as in a remote surgical system, the remote worksite having a manipulator with an end effector for manipulating an object at the workspace, such as a body cavity, a controller including a hand control at the control operator's station for remote control of the manipulator, an image capture device, such as a camera, and image output device for reproducing a viewable real-time image, the improvement wherein a position sensor associated with the image capture device senses position relative to the end effector and a processor transforms the viewable real-time image into a perspective image with correlated manipulation of the end effector by the hand controller such that the operator can manipulate the end effector and the manipulator as if viewing the workspace in true presence. Image transformation according to the invention includes translation, rotation and perspective correction.

28 Claims, 7 Drawing Sheets

U.S. PATENT DOCUMENTS

| | | | |
|---|---|---|---|
| 5,305,203 | 4/1994 | Raab | 364/413.13 |
| 5,313,306 | 5/1994 | Kuban et al. | 348/65 |
| 5,339,799 | 8/1994 | Kami et al. | 128/4 |
| 5,368,015 | 11/1994 | Wilk | 128/4 |
| 5,417,210 | 5/1995 | Funda | 128/653.1 |
| 5,597,146 | 1/1997 | Putman | 248/276.1 |
| 5,630,431 | 5/1997 | Taylor | 128/897 |
| 5,697,939 | 12/1997 | Kubota et al. | 606/130 |
| 5,754,741 | 5/1998 | Wang et al. | 395/56 |
| 5,762,458 | 6/1998 | Wang et al. | 414/1 |
| 5,808,665 | 9/1998 | Green | 348/65 |
| 5,817,084 | 10/1998 | Jensen | 606/1 |
| 5,855,553 | 1/1999 | Tajima et al. | 600/407 |
| 5,855,583 | 1/1999 | Wang et al. | 606/139 |
| 5,876,325 | 3/1999 | Mizuno et al. | 600/102 |
| 5,907,664 | 5/1999 | Wang et al. | 395/86 |

OTHER PUBLICATIONS

Hunter et al., "A teleoperated microsurgical robot and associated virtual environment for eye surgery" Presence: Teleoperators and Virtual Environments (1994) 2(4):265–280.

Kim et al., "A helmut mounted display for telerobotics" IEEE (1988) pp. 543–547.

Preising et al., "A literature review: Robots in medicine" IEEE Engineering in Medicine and Biology (1991) pp. 13–22.

Taubes et al., "Surgery in cyberspace" Discover (1994) 85–92.

Tsai et al., "A new technique for fully autonomous and efficient #D robotics hand–eye calibration".

Askew et al., "Ground Control Tesbed for Space Station Freedom Robot Manipulators," Proceedings of the Virtual Reality Annual International Symposium, Seattle, USA, Sep. 18–22, 1993 Institute of Electrical And Electronics Engineers, pp. 69–75.

Christensen et al., "Model Based, Sensor Directed Remediation of Underground Storage Tanks," Proceedings of the International Conference on Robotics and Automat, Sacramento, USA, Apr. 9–11, 1991, vol. 2 Institute of Electrical and Electronics Engineers, pp. 1377–1383.

Das et al., "Kinematic Control and Visual Display of Redundant Teleoperators," Proceedings of the International Conference on Systems, Man and Cybernetics, Cambridge, MA., USA, Nov. 14–17, 1989, pp. 1072–1077.

Hayati et al. "Remote Surface Inspection System," *Robotics and Autonomous Systems,* vol. 11, No. 1, May 1993, Amsterdam, NL, pp. 45–59.

Trivedi Mohan et al., "Developing Telerobotic Systems Using Virtual Reality Concepts," Proceedings of the 1993 IEEE/RSJ International Conference on Intelligent Robots and Systems, Yokohama, Japan, Jul. 26–30, 1993, pp. 352–359.

Alexander, III, Proc. of the $1^{st}$ CISM–ITOMM Symposium, Sep. 5–8, 1973, Springer–Verlag. Wien–New York. Impacts of Telemation on Modern Society.

NASA Tech Briefs, *Circle Reader Action No. 480.* (1991), Anthropomorphic Remote Manipulator.

Bergamasco et al., Advanced Interfaces for Teleoperated Biomedical Robots, Jun. 1989.

Toon, *Research Horizons,* (1993) pp. 22–23, Virtual Reality for Eye Surgery.

METHOD AND APPARATUS FOR TRANSFORMING COORDINATE SYSTEMS IN A TELEMANIPULATION SYSTEM

This application is a continuation of, and claims the benefit of priority from, U.S. patent application Ser. No. 08/783,644, filed Jan. 14, 1997, now U.S. Pat. No. 5,859, 934, which is a continuation application of Ser. No. 08/239086, filed May 5, 1994, now U.S. Pat. No. 5,631,973, issued May 20, 1997, the full disclosures of which are incorporated herein by reference. This application is also a continuation-in-part of, and claims the benefit of priority from, U.S. patent application Ser. No. 08/709,930 filed on Sep. 9, 1996. Now U.S. Pat. No. 5,808,665, which is a continuation of U.S. patent application Ser. No. 08/517,053 filed on Aug. 21, 1995 now abandoned, which is a continuation of U.S. patent application Ser. No. 07/823,932 filed on Jan. 21, 1992 now abandoned.

This invention was made with Government support under Grant No. 5-R01-GM44902-02 awarded by the National Institutes of Health. The Government has certain rights in the invention.

BACKGROUND OF THE INVENTION

This invention relates to telemanipulation using telepresence, and more particularly to applications of telemanipulation to laparoscopic surgery.

A telemanipulation system allows an operator to manipulate objects located in a workspace from a remote control operator's station. For example, in a laparoscopic abdominal surgery procedure, the patient's abdomen is insufflated with gas, and cannulas are passed through small incisions to provide entry ports for laparoscopic surgical instruments. Laparoscopic surgical instruments include an image capture means for viewing the surgical field and working tools, such as forceps or scissors. The working tools are similar to those used in open surgery, except that the working end of each tool is separated from its handle by an extension tube. The surgeon performs surgery by sliding the instruments through the cannulas and manipulating them inside the abdomen while referencing a displayed image of the interior of the abdomen. Surgery by telepresence, that is, from a remote location by means of remote control of the surgical instruments, is a next step. A surgeon is ideally able to perform surgery through telepresence, which, unlike other techniques of remote manipulation, gives the surgeon the feeling that he is in direct control of the instruments, even though he only has remote control of the instruments and view via the displayed image.

The effectiveness of telepresence derives in great measure from the illusion that the remote manipulators are perceived by the operator of the system to be emerging from the hand control devices located at the remote operator's station. If the image capture means, such as a camera or laparoscope, are placed in a position with respect to the manipulators that differs significantly from the anthropomorphic relationship of the eyes and hands, the manipulators will appear to be located away from the operator's hand controls. This will cause the manipulators to move in an awkward manner relative to the viewing position, inhibiting the operator's ability to control them with dexterity and rapidity. However, it is often unavoidable in applications such as laparoscopic surgery to move the laparoscope in order to obtain the best possible image of the abdominal cavity.

Thus, a technique is needed for providing to the operator the sense of direct hand control of the remote manipulator, even in the presence of a substantially displaced imaging device, such that the operator feels as if he is viewing the workspace in true presence.

SUMMARY OF THE INVENTION

According to the invention, in a telemanipulation system for manipulating objects located in a workspace at a remote worksite by an operator at an operator's station, such as in a remote surgical system, the remote worksite having a manipulator or pair of manipulators each with an end effector for manipulating an object at the workspace, such as a body cavity, a controller including a hand control at the control operator's station for remote control of the manipulators, an image capture means, such as a camera, for capturing in real-time an image of the workspace, and image producing means for reproducing a viewable image with sufficient feedback to give the appearance to the control operator of real-time control over the object at the workspace, the improvement wherein means are provided for sensing position of the image capture means relative to the end effector and means are provided for transforming the viewable real-time image into a perspective image with correlated manipulation of the end effector by the hand control means such that the operator can manipulate the end effector and the manipulator as if viewing the workspace in substantially true presence. By true presence, it is meant that the presentation of an image is a true perspective image simulating the viewpoint of an operator. Image transformation according to the invention includes rotation, translation and perspective correction.

The invention will be better understood by reference to the following detailed description in connection with the accompanying drawings.

DESCRIPTION OF SPECIFIC EMBODIMENTS

Figure 1A:
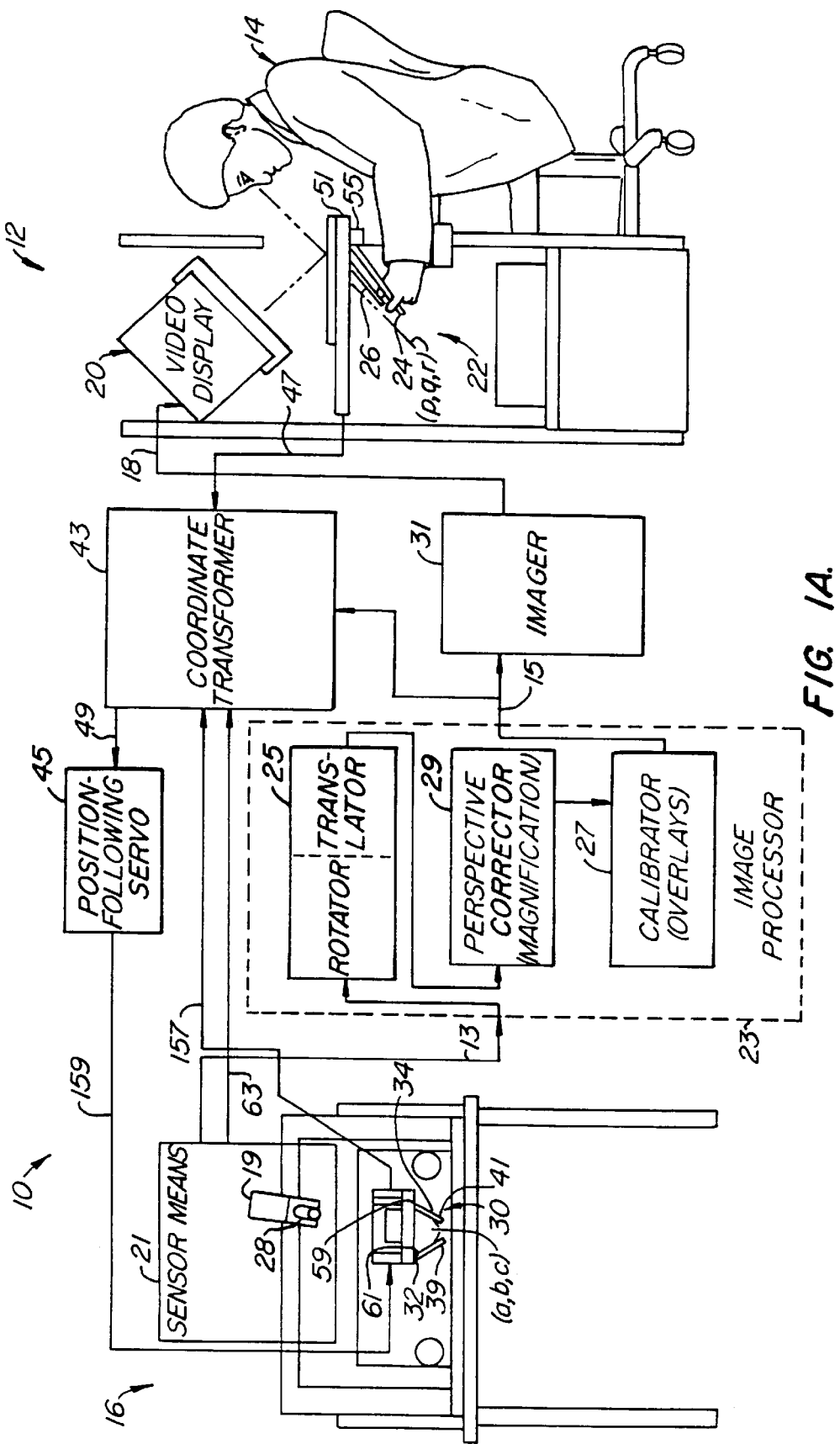
FIG. 1A is a side view of a remote operator station and of a worksite station in a telemanipulation system according to the present invention.

FIG. 1A shows a telemanipulation system 10 according to the present invention with a remote operator station 12 where an operator 14 (a surgeon, for example) can perform telemanipulation on an object at a worksite station 16. The remote station 12 includes a video display 20 for the operator 14 to view the worksite and an apparent workspace 22 where the operator 14 carries out the actual manipulations by grasping hand control means 24, 26, such as surgical instrument handles, which are connected to position sensors 51, 55. The worksite station 16 includes an image capture means 19, including a sensor means 21 with camera lens 28 of a camera or endoscope and understanding that there is an image capture means 19 associated with that lens, which captures an image of an object located in the workspace 30. (An endoscope would be within the body cavity.) The manipulators 32, 34 allow manipulation of the object in the workspace 30 correlated with a displayed image by use of end effector means 39, 41.

The image captured at worksite 16 is transmitted through a number of stages which present to operator 14 a real-time image of the object in the workspace 30. In particular, sensor means 21, including optical image capture means 19, provides a view of the manipulators 32, 34 through a camera lens 28, passing such image information via path 13 to an image processor 23. In addition, image sensor position information (camera position) may be passed on path 63 to coordinate transformer 43. (For a fixed camera, the camera position information can be preset). Further, mechanical position sensing means 59, 61 sense the position of manipulators 32, 34 mechanically, passing on the position information to coordinate transformer 43 via path 157.

The image processor 23 includes a rotation and translation means 25, a perspective correction means 29 and a calibration means 27. The rotator is for rotating the image and the translator is for shifting the rotated image. The perspective corrector 29 is primarily for magnifying the image and may include some tilt correction. The calibrator 27 may have various functions, depending upon the type of image input. It is in particular used to calibrate the image to a known reference coordinate system to enable an operator to coordinate motions of the hand controls and the manipulators. After the image has undergone transformation through one or more of these function blocks, the pixel data is passed on path 15 to an imager 31 which drives a video display 20, which in this embodiment is a monoscopic device, and data about the image is passed on to the coordinate transformer 43, whereby any processed image data potentially affecting control of the manipulators (e.g., magnification, rotation, translation) is made available for the control of the manipulators. The details of the processes which may be affected are explained hereinbelow, particularly with respect to calibration.

The coordinate transformer 43 is the principal processor of position information. Camera position information, manipulator position information, and hand control position information are received and processed therein. In particular, the positions of hand controls 24, 26 are sensed by position sensors 51, 51 and passed via path 47 to coordinate transformer 43. After transformation and processing in coordinate transformer 43, control information is applied to position-following servo 45, which drives and controls manipulators 32, 34 with end effectors 39, 41. The operation of each of these blocks will be described in further detail.

In operation, the camera lens 28 captures the image of the object in the actual workspace 30 in a specific orientation on image capture means 19. The video display 20 displays this image so that the operator 14 can view the object as it is manipulated. The operator 14 may then grasp hand control means 24, 26 located in the apparent workspace 22 to carry out the desired manipulations. The hand control means 24, 26 at remote station 12 under instruction of the position-following servo 45 control the manipulators 32, 34 at worksite station 16, which actually manipulate the object in workspace 30. The actual workspace 30 is thus effectively projected back to the remote operator 14 to create the illusion that he is reaching and looking directly into it and controlling the object located in workspace 30. Properly projected, this results in natural and spontaneous control motions by the operator 14, even if he is located in an another room or another extremely remote location.

The problems addressed by the present invention arise from the situation where the camera lens 28 is not placed at the same position in the real workspace 30 relative to the manipulators 32, 34 as the eyes of the control operator viewing the projected image in the "apparent" workspace 22 relative to the hand control means 24, 26. A solution is provided by the present invention.

Figure 1B:
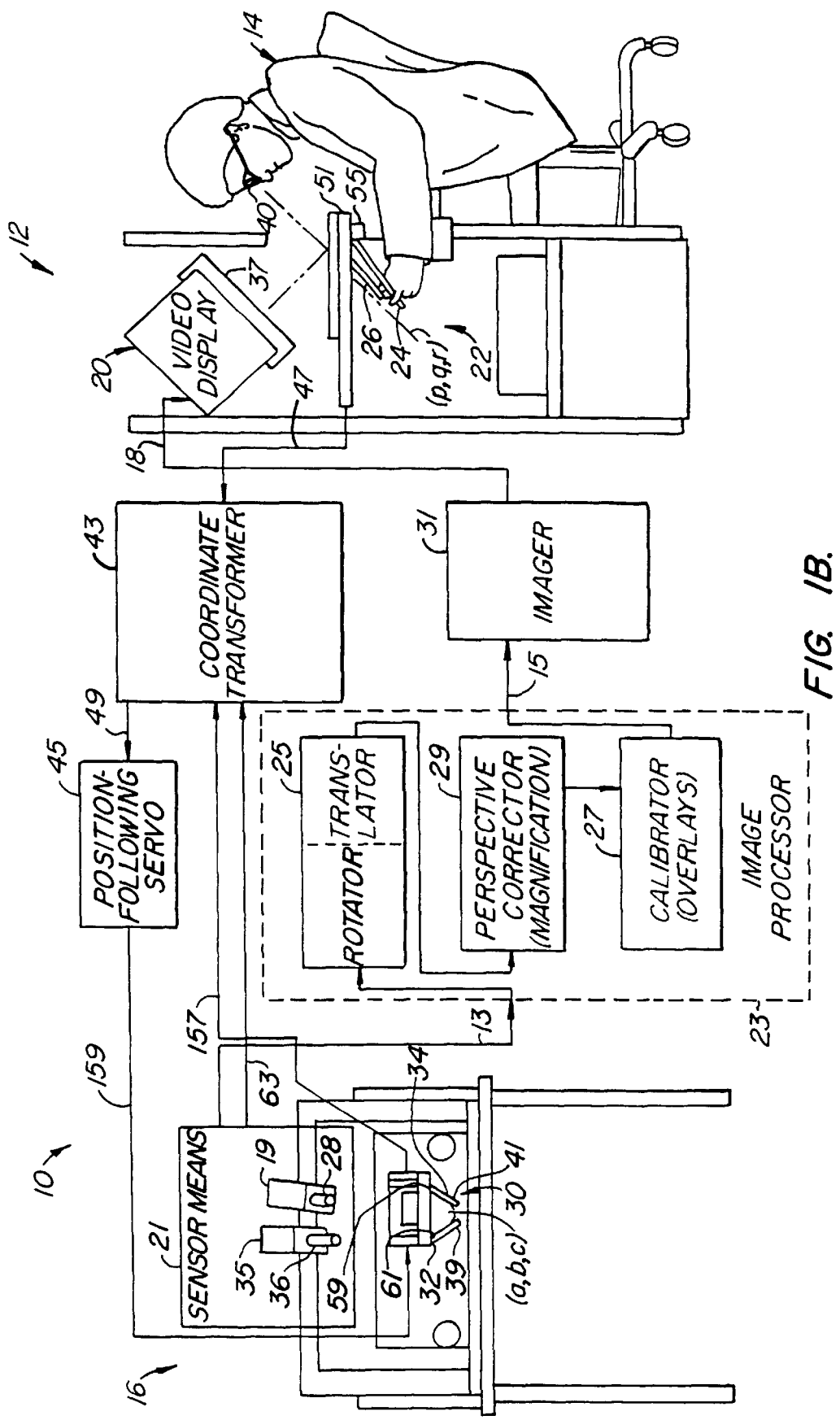
FIG. 1B is a perspective view of a remote operator station and a worksite station adapted for stereoscopic viewing in a telemanipulation system according to the present invention.

The telemanipulation system according to the present invention can also be adapted to accommodate stereoscopic viewing. FIG. 1B shows all the elements of FIGS. 1A, with the addition of a second camera lens 36 and image capture means 35. The two camera lenses 28 and 36 can be separated by about 10°, which is the same interocular viewing disparity that one experiences when viewing a visual field at 40 cm separation. The stereo image is displayed on a stereo video display monitor 38 (e.g. using an electronically switched polarizer 37 over the screen) and viewed through cross-polarized stereoscopic lenses 40, thus offering a natural image to the remote operator 14 so that the operator experiences the correct visual feedback when reaching and looking directly into the actual workspace 30 and directly manipulating the object located therein. The details of the system are explained hereinafter.

Figure 2:
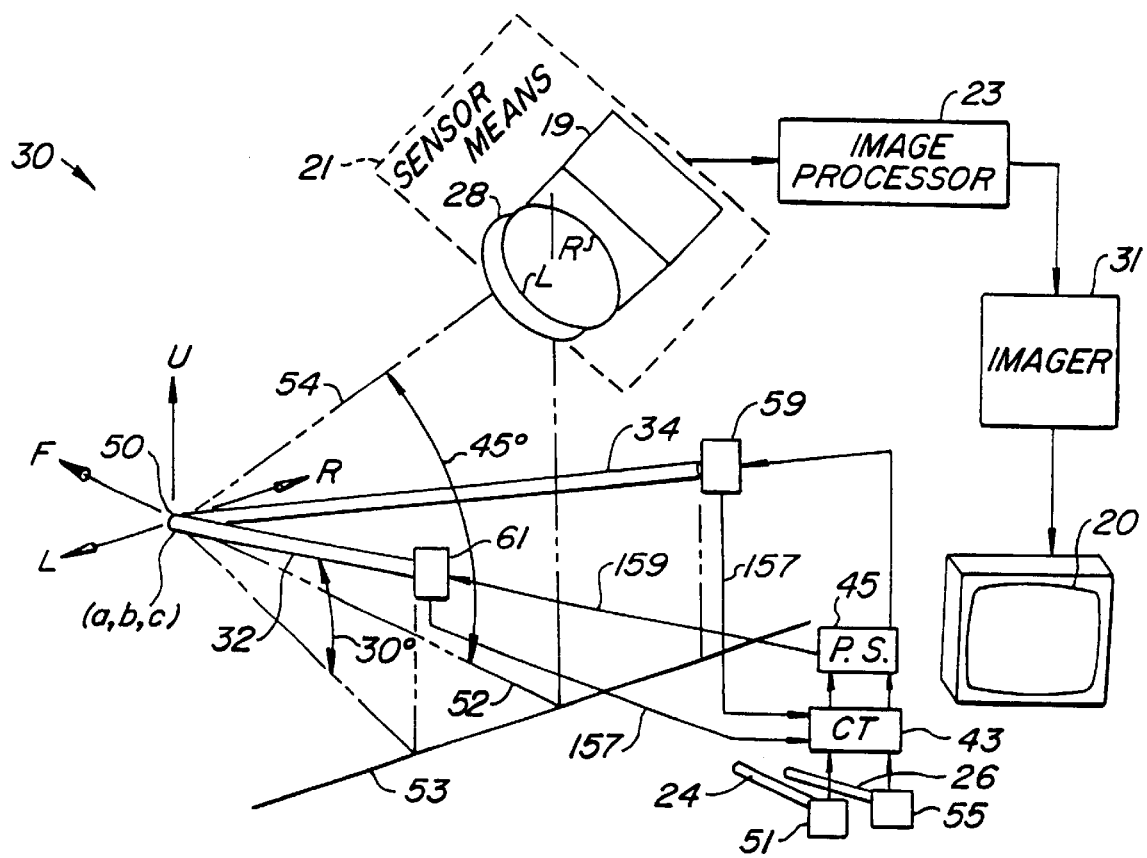
FIG. 2 is a diagrammatic perspective view of a specific embodiment of the invention wherein the image capture means is centered and normalized relative to the viewpoint of an operator using the manipulators.

FIG. 2 is a diagrammatic perspective view of the elements of the worksite station 16 in workspace 30 of the telemanipulation system, showing features of FIG. 1 which are in a control loop. The system an operator at a remote station to manipulate objects located at a centerpoint 50 in the workspace 30. In the monoscopic system, sensor means 21 with camera lens 28 and image capture means 19 captures a real-time image of the object. The operator 14 uses dual hand control means 24, 26 to control left manipulator 32 and right manipulator 34, respectively, which allow remote manipulation of the object at the workspace 30. For hand control means 24, 26 and manipulators 32, 34, there is in this example a fixed pivot point about which bidirectional angular motion can be effected, together with a telescopic-like extension capability for each of the manipulators and hand controllers. The correlation between the hand control means 24, 26 and the manipulators 32, 34, combined with the image captured by the camera lens 28, provide sufficient feedback to give the appearance to the control operator of real-time control over the object at the workspace (further improvement is possible with tactile feedback). Both left manipulator 32 and right manipulator 34 are in this example raised 30° with respect to an arbitrary plane of orientation, including a centerline axis 52 of the workspace 30, to simulate a typical positioning of an object in the real local workspace 30.

In operation, camera lens 28 is at the 0° lateral position with respect to the centerline axis 52, such that the camera lens 28 is between left manipulator 32 and right manipulator 34. The face of the camera lens 28 is raised at for example a 45° angle with respect to the plane containing centerline axis 52 and baseline 53. This camera position and orientation is a close approximation to the actual eye position with respect to the manipulators 32 and 34 and represents a base or reference position. The image captured by the camera lens 28 appears as if the operator were looking at the centerpoint 50 while standing over the manipulators 32 and 34 with a 45° angle view into the workspace. Both left manipulator 32 and right manipulator 34 appear in the bottom of the displayed image (proximal to the operator's hand controls), evoking a strong sense of telepresence, which means that the operator senses direct control of manipulators 32 and 34, allowing control with dexterity and rapidity, particularly where there is tactile feedback from the manipulators 32, 34 to the hand control means 24, 26.

Figure 3:
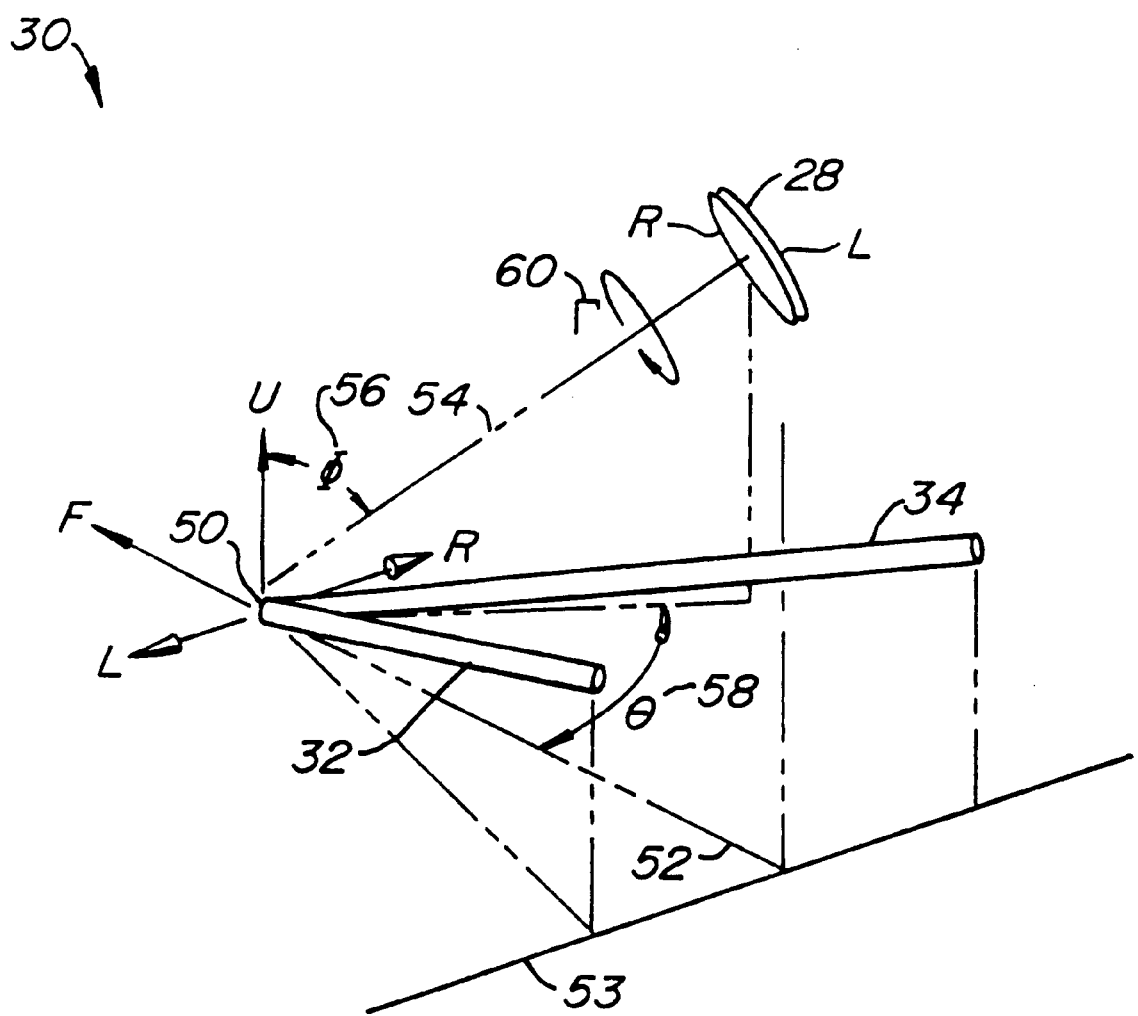
FIG. 3 is a diagrammatic perspective view of a specific embodiment of the invention wherein the image capture means is laterally displaced relative to the viewpoint of an operator using the manipulators.

In a telemanipulation application in which positioning of elements is difficult due to obstructions, it is often necessary to move the camera lens 28 to different positions result in a different view of the object at the centerpoint 50. Referring to FIG. 3, a diagrammatic perspective view of the elements in workspace 30 of the worksite station 16 of a monoscopic telemanipulation system is shown in which the camera lens 28 position is rotated by angle θ 58 laterally in the horizontal plane away from the centerline axis 52. After rotation of the camera lens 28, left manipulator 32 and right manipulator 34 are still inclined downward at a 30° angle relative to the plane containing centerline axis 52 and baseline 53, and the camera lens 28 is still positioned at an angle θ above the plane formed by centerline axis 52 and baseline 53. In order to evoke a sense of telepresence in the operator similar to the case in which the camera lens 28 is positioned directly over manipulators 32 and 34 (as in FIG. 2), according to the invention, the captured image projected by the camera lens 28 is rotated about visual axis 54 through the center of the camera lens 28. This compensates for rotation about "vertical" axis U to effect a static reorientation of the apparent manipulator positions.

Figure 4:
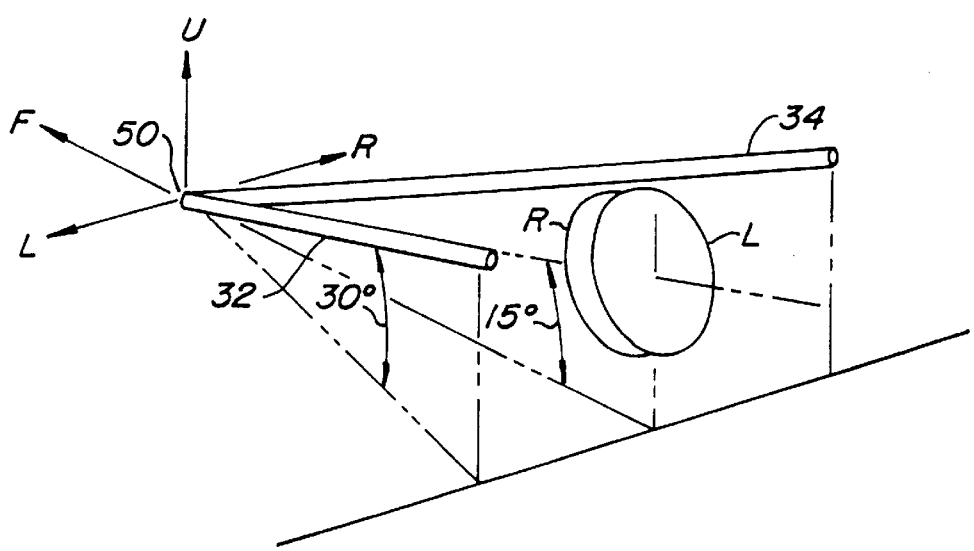
FIG. 4 is a diagrammatic perspective view of a specific embodiment of the invention wherein the image capture means is at a lower position relative to the viewpoint of an operator using the manipulators.

It should be understood that camera lens 28 and image capture means 19 enjoy a full range of rotation about vertical axis U, and that the angles relative to reference planes and the like of the manipulators and the camera are dictated by the constraints of the operating environment. Additionally, camera lens 28 may be positioned at different angles relative to the plane formed by centerline axis 52 and baseline 53. For example, FIG. 4 shows camera lens 28 positioned at an elevation of 15° above the (arbitrary) reference plane formed by centerline axis 52 and baseline 53. In this alignment, camera lens 28 is below manipulators 32, 34.

If the image is purely monoscopic as depicted in FIG. 1A, the system can effect static reorientation of the manipulators 32 and 34 about an axis 54 through a point, specifically center point 50, by rotating the digital image through rotation means 25. FIG. 3 shows the relevant angles of rotation. Angle Φ 56 denotes the angle of declination of the visual axis 54 of camera lens 28 below vertical axis U. Angle θ 58 denotes the rotation of camera lens 28 position in the horizontal plane (formed by lines 52, 53) away from centerline axis 52 relative to the centerpoint 50.

Rotation means 25 effects static realignment of the manipulators by rotating the real-time image pixel-by-pixel by an angle approximately equal to −θ, according to known methods. After this operation is complete, the left manipulator 32 and right manipulator 34 appear in the bottom of the displayed image (lower half of the projected screen). The camera lens 28 remains stationary, and the displayed image is rotated through image manipulation. Note that if hand control means 24, 26 at the operator's station are positioned above the viewpoint of the control operator, the rotation of the displayed image will correct the displayed image to the point where the manipulators appear in the top of the displayed image (upper half of the projected screen). In either case, the transformation of the displayed image allows the operator to view the manipulators as if emerging from the operator's hand controls. The remapping of the image is effected before actual control can be effected.

In addition to effecting static realignment through digital image transformation, transformation means 25 may effect dynamic synchronization of apparent manipulator tip positions with hand control positions by performing the following coordinate transformation on the video image data. The actual position of the manipulator tips in the workspace 30 can be transformed to an apparent position in the displayed image so that the manipulators will appear to move as though rigidly connected to the operator's hand controls. The altering of the apparent position of the manipulator tips improves the dexterity of the operator in handling the object in the workspace 30. Because the end point of the end effector of the manipulator is known, the point (a,b,c) can be related to the angular position and length of the manipulator, and the point (p,q,r) can be related to the same parameters relative to the hand control using well-known trigonometric relationships between vectors and their endpoints. Thus:

$$\begin{vmatrix} p \\ q \\ r \end{vmatrix} = \begin{vmatrix} \cos\theta' & \sin\theta' & 0 \\ -\sin\theta' & \cos\theta' & 0 \\ 0 & 0 & 1 \end{vmatrix} \begin{vmatrix} \cos\Phi & 0 & \sin\Phi \\ 0 & 1 & 0 \\ -\sin\Phi & 0 & \cos\Phi \end{vmatrix} \quad \text{(Eq. 1)}$$

$$\begin{vmatrix} \cos\theta & \sin\theta & 0 \\ -\sin\theta & \cos\theta & 0 \\ 0 & 0 & 1 \end{vmatrix} \begin{vmatrix} a \\ b \\ c \end{vmatrix}$$

In connection with the transformation associated with the above equation, the image is rotated by an angle θ' selected by the operator to bring the apparent position of the manipulators into substantial registration with the hand controls. It is an observation that angle θ'≈−θ. This transformation describes the relationship between the position of the point represented by the end effector means at (a,b,c) (for either end effector means) relative to the point (p,q,r) of the corresponding tip of the manipulator in the apparent workspace in the displayed image on video display 20.

Another method of achieving static reorientation of manipulator positions is to rotate the image capture means about its visual axis. Referring again to the monoscopic system depicted in FIG. 1A and FIG. 3, camera lens 28 is rotated about its own visual axis 54, an axis normal to the plane of the camera lens 28, to the point where left manipulator 32 and right manipulator 34 appear in the bottom of the displayed image (lower half of the projected screen). Note again that if hand control means at the operator's station are positioned above the viewpoint of the control operator, the rotation of camera lens 28 and image capture means 19 will correct the displayed image to the point where the manipulators appear in the top of the displayed image (upper half of the projected screen).

Figure 5A:
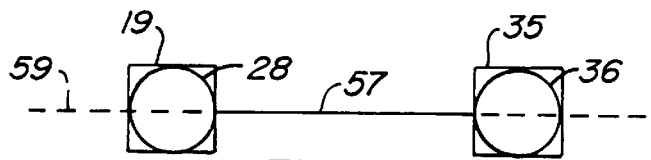
FIG. 5A is a front elevational view of the lenses of a stereoscopic image capture means where the lenses are in a normalized position relative to the viewpoint of an operator using the manipulators.
Figure 5B:
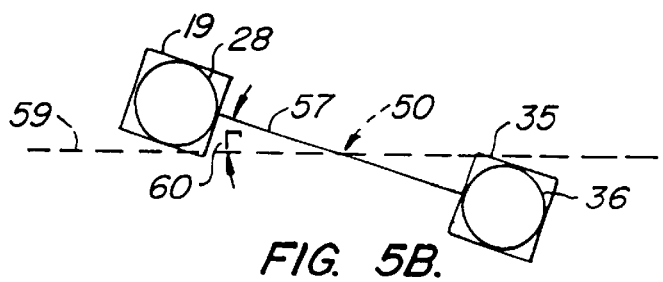
FIG. 5B is a front elevational view of the lenses of a stereoscopic image capture means where the lenses are rotated relative to the viewpoint of an operator using the manipulators.

To preserve the stereoscopic effect, in the case of stereoscopic imaging, as depicted in FIG. 1B, rotations cannot be done about separate axes through each camera lens, but (referring to FIG. 5A and FIG. 5B) must be done in concert about a single axis offset from either lens. Specifically, rotation is done normal to center axis 57 passing through the centerpoint 50 and an arbitrary point on center axis 57 between the stereoscopic camera lenses 28 and 36 (FIG. 5A & 5B). This axis is similar to the visual axis 54 described in connection with FIG. 2. Referring to FIG. 5A, the lenses of a stereoscopic device are shown in their initial position. Center axis 57 shows the fixed relation of each lens of the camera pair and is parallel to a reference axis 59 parallel to an axis in the plane formed by manipulators 32, 34 intersecting at the centerpoint 50, where the axis is normal to a line bisecting the manipulators and passing through the centerpoint 50. In order to reorient the displayed image through rotation of the image capture means, center axis 57 is canted relative to a reference plane 59 passing through centerpoint 50, which plane includes reference axis 59, as shown in FIG. 5B.

There is a limitation on the amount of visually acceptable rotation of the stereoscopic image capture means 19, 35 and the elevation of the image capture means 19, 35 relative to the plane of the manipulators 32, 34. The elevation cannot be so great as to make it impossible to change the relative view angle of each of the two manipulators relative to one another. Clearly, if angle Φ equals 90° elevation (where the viewing axis 54 lies in the reference plane formed by lines 52 and 53), no useful change in the relative view angle will be achieved by rotating the image. At other angles of elevation, the limitation depends on the separation angle of the manipulators 32, 34 and secondarily on the separation of the stereoscopic lenses 28, 36.

In addition to achieving static reorientation of manipulator positions by rotation of the camera lens 28, the system can effect a dynamic realignment by performing a coordinate transformation through translation means 25. The actual position of the manipulator tips in the workspace 30 can be transformed to an apparent position in the displayed image so that the manipulators will appear to move as though rigidly connected to the operator's hand controls. The altering of the apparent position of the manipulator tips improves the dexterity of the operator in handling the object in the workspace 30.

Figure 8:
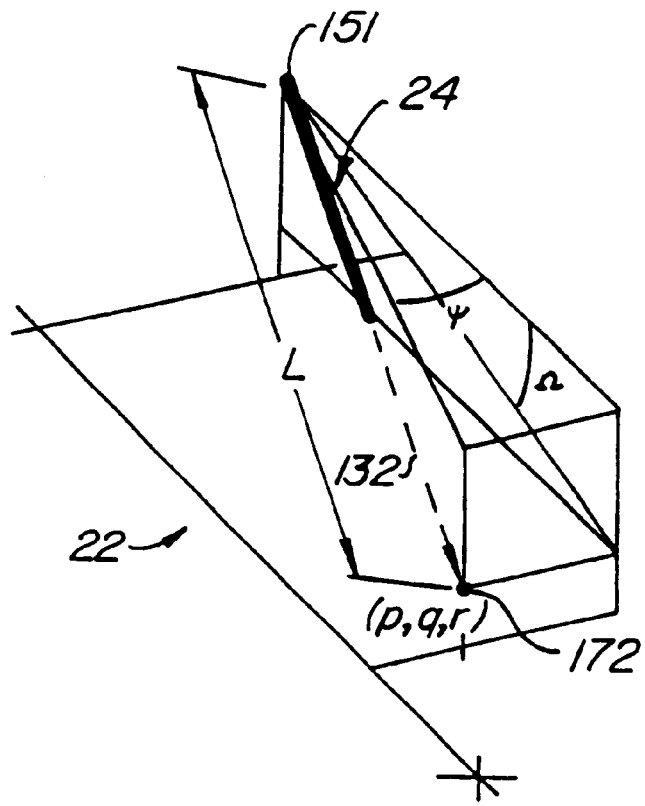
FIG. 8 is a geometric depiction of the image of a manipulator as a projection of a hand control.
Figure 9:
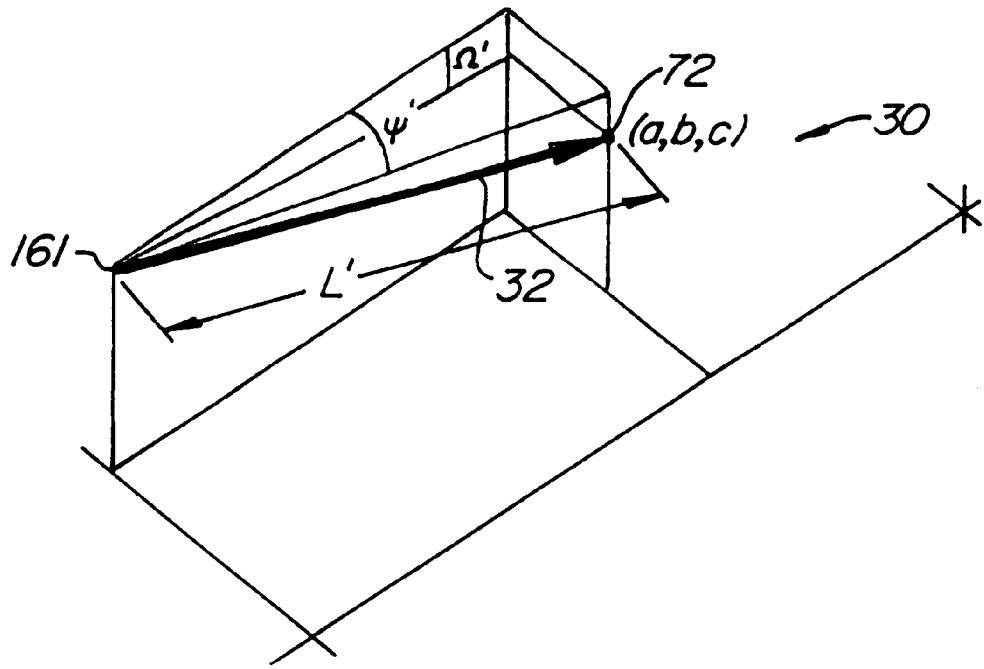
FIG. 9 is a geometric depiction of the actual manipulator whose image is depicted in FIG. 8.

FIG. 8 and FIG. 9 depict the image 132 of a manipulator (32) and an actual manipulator 32, respectively, relative to a hand control 24. In this example, and comparing FIG. 2, manipulators and corresponding controllers represented by hand controls are of a type utilizing a single pivot point 151, 161 in connection with the position sensors 51, 61 with two dimensional pivot about the point(s) and extension along the axis of the manipulator 32. Other motions consistent with these actuations, such as longitudinal rotation of the manipulator about its axis is contemplated by the invention. With reference to FIG. 8 and FIG. 9, movement of the hand control 24 causes the manipulator tip 72 to move to a new point (a,b,c) in workspace 30 such that the image 132 of the manipulator tip 172 moves to a new point (p,q,r) in the apparent workspace 22, that point appearing in the view of the operator to be at the extended end of the hand control 24. It may be preferable to express the servo commands relating the hand control and the corresponding manipulator in their polar coordinate systems (Ω, ψ, L) and (Ω', ψ', L'). These polar coordinates and their respective points in Cartesian coordinate systems are related by well-known polar to Cartesian transformations.

Referring again to FIG. 3, the specific angles of rotation used in calculating the coordinate transformation are shown. Angle Φ 56 denotes the angle of declination of the visual axis 54 of camera lens 28 below vertical axis U. Angle θ 58 denotes the rotation of camera lens 28 in the horizontal plane away from centerline axis 52 relative to the centerpoint 50 in the workspace 30. Angle Γ 60 denotes the rotation of camera lens 28 about its visual axis 54.

In operation of a monoscopic telemanipulation system, camera lens 28 and image capture means 19 are rotated about visual axis 54 as described above. The coordinates (a,b,c) in a reference orthogonal Cartesian coordinate system of the three-dimensional workspace 30 define the actual position of the tip of a manipulator, such as left manipulator 32. The following matrix equation relates the desired apparent position (p,q,r in orthogonal Cartesian space) of the manipulator tip in the displayed image in video display 20 to the actual position (a,b,c) of the manipulator tip in the workspace 30:

$$\begin{vmatrix} p \\ q \\ r \end{vmatrix} = \begin{vmatrix} \cos\Gamma & \sin\Gamma & 0 \\ -\sin\Gamma & \cos\Gamma & 0 \\ 0 & 0 & 1 \end{vmatrix} \begin{vmatrix} \cos\Phi & 0 & \sin\Phi \\ 0 & 1 & 0 \\ -\sin\Phi & 0 & \cos\Phi \end{vmatrix} \quad \text{(Eq. 2)}$$

$$\begin{vmatrix} \cos\theta & \sin\theta & 0 \\ -\sin\theta & \cos\theta & 0 \\ 0 & 0 & 1 \end{vmatrix} \begin{vmatrix} a \\ b \\ c \end{vmatrix}$$

When the manipulator tip is displayed at a position (p,q,r) in the displayed image in video display 20, the manipulator will appear to the operator as if it is actually at the end of the operator's rigid hand control device. The coordinate transformation improves the ease with which the operator can handle objects in the workspace using a telemanipulation system.

In the case of stereoscopic imaging, the stereo image capture means 19, 35 is rotated relative to a reference axis 59 parallel to an axis in the plane formed by manipulators 32, 34 intersecting at the centerpoint 50, where the axis is normal to a line bisecting the manipulators and passing through the centerpoint 50, as shown in FIG. 5B. Angle Γ 60 measures the amount of rotation of the stereoscopic lenses 28, 36, and its value can be used in Eq. 2 to calculate the proper coordinate transformation for stereoscopic viewing.

Figure 6A:
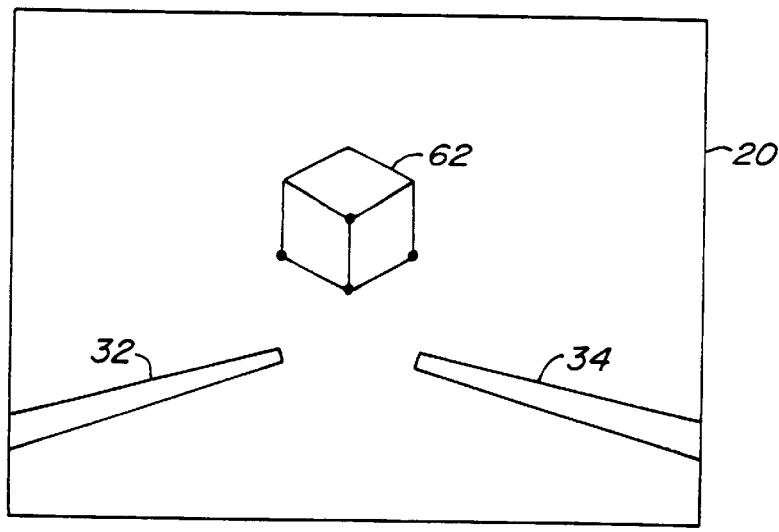
FIG. 6A is a top plan view of an image of a remote manipulator in a telemanipulation system that shows a superimposed stereographic four-point coordinate element prior to calibration.
Figure 6B:
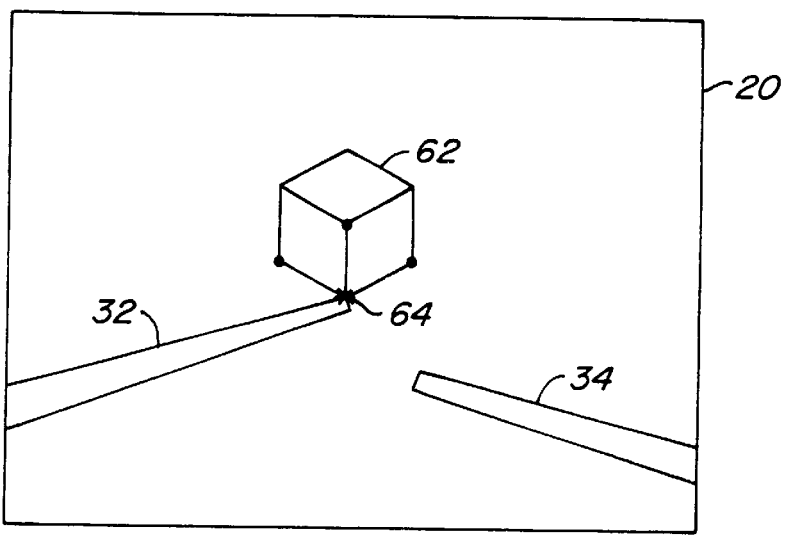
FIG. 6B is a top plan view of an image of a remote manipulator in a telemanipulation system that shows a superimposed stereographic four-point coordinate element after calibration.

In order to ensure that the movements of the manipulators 32, 24 in workspace 30 properly track the movements of the hand controls 24, 26 in the operator's apparent workspace 22 even without complete knowledge of all angles and positions, the operator can establish a calibration reference for manipulators 32, 34 as they are viewed in the displayed image in video display 20 in connection with the position-following servo. Referring to FIG. 6A, which shows the image displayed in video display 20, a four-point coordinate graphic element 62 for example in the form of a tetrahedron or cube structure in three-dimensional view may be superimposed in three-dimensional space on the stereo image display, providing a coordinate reference in the three-dimensional image space. To calibrate the position of a single manipulator with respect to its corresponding hand control, the system "opens" the control loop, and the operator 14 moves hand control 24, for example, while observing the motion of the tip of manipulator 32, steering the tip until it appears to be touching a first reference point 64 of superimposed graphic element 62, as shown in FIG. 6B. (Since the motion of the hand control and manipulator tip have not yet been coordinated, the alignment of the tip with the first reference point may require very deliberate effort.) The operator 14 then indicates to the system that superposition of manipulator and reference point has been achieved (e.g., a "set" signal is sent to the system).

The system then locks the manipulator 32 into place, opens the control loop by decoupling it from the hand control 24 and instructs the operator 14 to release the hand control 24. The system adjusts the extension L (FIG. 8 and 9) of the hand control to match that of the manipulator L', by inserting the offset $\sigma_3$=L−L', so that when the control loop is closed, there will be no reactive motion by either device. That is, the apparent extension positions of the hand control 24 and manipulator 32 must be identical when compared in the control loop. The system then closes the control loop and unlocks the manipulator 32, returning control to the operator 14.

The operator then moves the hand control about its pivot point to an angular orientation ($\Psi,\Omega$) at which the operator senses that the image of the manipulator appears to emerge from the operator's hand control. Similar to the process described above, the system computes transformations which ensure that there will be no reactive motion by either master or slave when the control loop is closed. The system calculates angular offsets $\sigma_1=\Psi-\Psi'$ and $\sigma_2=\Omega-\Omega'$ and transforming the apparent position of the master or the slave prior to closing the control loop. The system now records the positions in three-dimensional space of the hand control master ($\Psi_1, \Omega_1, L_1$) and the manipulator slave ($\Psi'_1, \Omega'_1, L'_1$).

The operator repeats the elements of this process with the remaining reference points of the superimposed graphic element 62. The system may then derive and install the following linearized equation relating incremental changes in the position of the hand control masters 24, 26 to incremental changes in the position of the manipulator slaves 32, 34, using the data sets to determine the coefficients of the equations relating the positions:

$$\Delta\Omega'=k_{11}\Delta\Omega+k_{12}\Delta\Psi+k_{13}\Delta L$$

$$\Delta\Psi'=k_{21}\Delta\Omega+k_{22}\Delta\Psi+k_{23}\Delta L$$

$$\Delta L'=k_{31}\Delta\Omega+k_{32}\Delta\Psi+k_{33}\Delta L$$

The solution to the above linearized equation is as follows:

$$\begin{vmatrix} k_{11} & k_{12} & k_{13} \\ k_{21} & k_{22} & k_{23} \\ k_{31} & k_{32} & k_{33} \end{vmatrix} = \begin{vmatrix} \Delta\Omega'_1 & \Delta\Omega'_2 & \Delta\Omega'_3 \\ \Delta\Psi'_1 & \Delta\Psi'_2 & \Delta\Psi'_3 \\ \Delta L'_1 & \Delta L'_2 & \Delta L'_3 \end{vmatrix} \begin{vmatrix} \Delta\Omega_1 & \Delta\Omega_2 & \Delta\Omega_3 \\ \Delta\Psi_1 & \Delta\Psi_2 & \Delta\Psi_3 \\ \Delta L_1 & \Delta L_2 & \Delta L_3 \end{vmatrix}^{-1} \quad \text{(Eq. 3)}$$

The system installs these coefficient values in the coordinate transformer 43 which controls servo 45, with appropriate offsets $\sigma_1, \sigma_2$ and $\sigma_3$, so that there is no reactive motion when the loop is closed.

In an alternative embodiment, calibration of the manipulators is achieved through virtual movement with the assistance of the system. Referring to FIG. 6B, the system moves manipulator tip 32, rather than the operator guiding the manipulator tip 32, to one of four defined points in the three-dimensional workspace 30, such as reference point 64 as seen by the operator. Using the hand control 24, the operator 14 then dynamically calibrates the position of the manipulator 32 by steering an overlaid graphic dot until it appears superimposed on the manipulator tip 32. The operator 14 then indicates to the system that superposition of manipulator tip 32 and reference point 64 has been achieved, and the coordinates of the manipulator 32 and hand control 24 are recorded. The process is repeated for the remaining reference points, after which the system derives and installs a coordinate transformation formula in the coordinate transformer 43, as described in the above embodiment.

In actual practice, it is preferable for the surgeon, rather than the system, to initiate the calibration process if the invention is being used in laparoscopic surgery. During surgery, the calibration process is being carried out within a patient's abdomen, where there is little room to maneuver. Hence, automatic movements of the manipulator, however small, may be considered less desirable than operator-controlled movements.

Another method for evoking a sense of telepresence in a telemanipulation system involves the use of a specific coordinate transformation to compensate for other changes in the displayed image, such as a lateral shift or a scale change. The camera may undergo a lateral or angular displacement, causing the displayed image to shift. In addition, the camera may be capable of magnifying the object in the workspace, which causes a scale change and a displacement of the apparent pivot point of the manipulator.

Figure 7A:
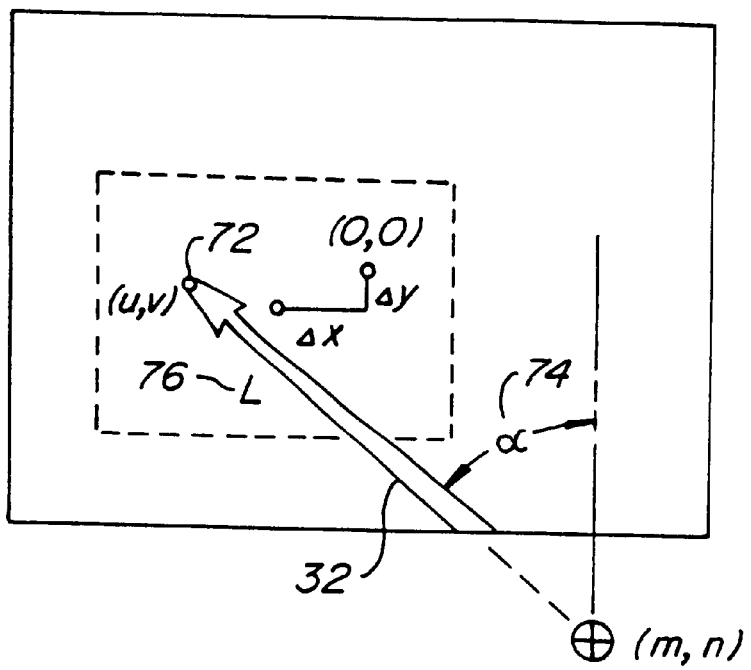
FIG. 7A is a top plan view of an image of a remote manipulator in a telemanipulation system that shows the angle of displacement in the horizontal of the image capture means relative to the manipulators.
Figure 7B:
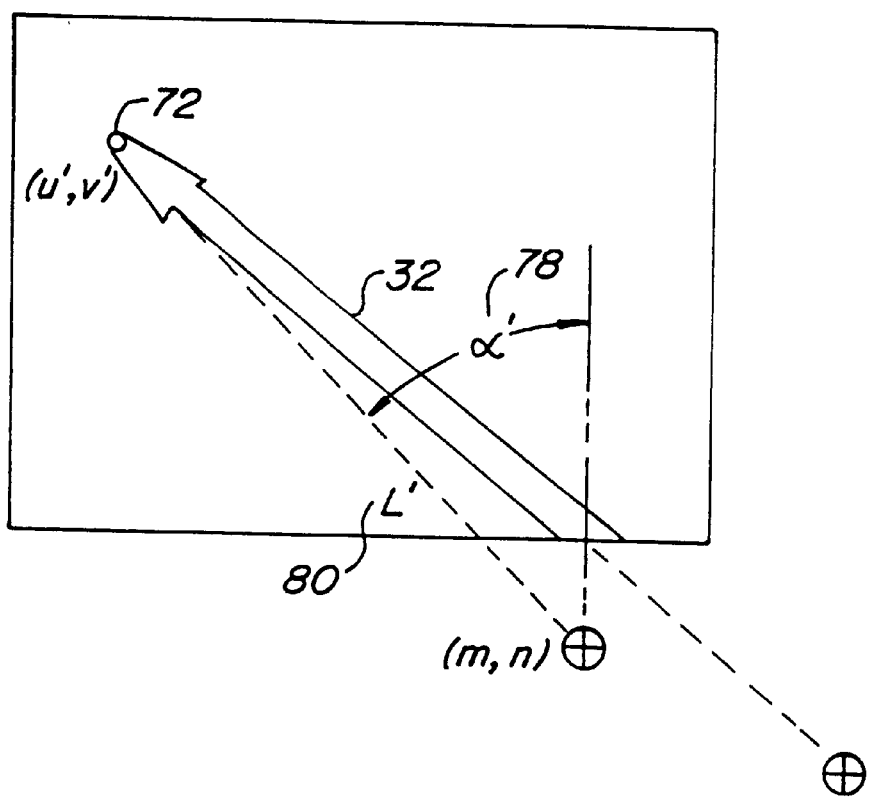
FIG. 7B is an enlarged view of a portion of FIG. 4A that shows the combined effect on the position of the end effector of a manipulator after a lateral shift.

FIGS. 7A and 7B show the combined effect of a lateral shift of the image and a scale change brought about by magnification of the image. FIG. 7A shows a portion of the displayed image, including a manipulator 32, in a two-dimensional field. The center of the image is at coordinates (0,0). The operator experiences the best possible sense of telepresence if the manipulator tip 72 at coordinates (u,v) in the image field appears to move as if it were rigidly attached to the control device in the operator's hand. The control device is pivoted at point (m,n) in the figure. The manipulator lies at an angle $\alpha$ 74 to the y-axis, and the distance from pivot point (m,n) to manipulator tip (u,v) is length L 76.

FIG. 7B shows what the operator would see if the image were magnified by a factor M. The center of the image is shifted laterally by a distance of $\Delta x$ and $\Delta y$, and the new apparent coordinates of the manipulator tip 72 are (u',v'). In order to ensure a desired level of telepresence, angle $\alpha$ 74 and length L 76 are remapped through perspective correction means 29 in the displayed image to give the operator the impression that the manipulator tip 72 is still rigidly attached to the hand control device. The following pair of equations describe the remapping of angle $\alpha$ 74 into angle $\alpha'$ 78 and length L 76 into length L' 80:

$$\alpha'=\arctan\,[(u'-m)/(v'-n)] \text{ and}$$

$$L'=[(u'-m)^2+(V'-n)^2]^{\frac{1}{2}}$$

where:

$$u' = M(u-\Delta x) \qquad v' = M(v-\Delta y) \qquad \text{and where}$$

$$u = L(\sin\alpha)+m \qquad v = L(\cos\alpha)+n$$

When $\alpha$ and L are remapped according to the above equations, the manipulator tip 72 appears in the displayed image to move as if it were rigidly connected to the operator's hand control device.

The above relationships can be extended to include transformations in three dimensions in order to compensate for displacement of the manipulators when the camera lens 28 is rotated about its own visual axis 54, as in the embodiment described with respect to FIG. 3. In all cases, the desired goal of maintaining the perceived plane containing the two manipulators coincident with the plane of the two hand controls is achieved.

The invention has now been explained with reference to specific embodiments. Other embodiments will be apparent to those of ordinary skill in the art upon reference to the present description. For example, the invention can be extended to articulated manipulators with multiple points of rotation and translation or with pivot points at locations not physically attached to the manipulators. It is therefore not intended that this invention be limited, except as indicated by the appended claims.

What is claimed is:

1. A telesurgical system including,
   a work station having an endoscope for capturing an image of a surgical site and at least one manipulator arranged to perform at least part of a surgical procedure at the surgical site;
   a remote operator station having an image display device operatively associated with the endoscope to display the image captured by the endoscope and at least one hand control operatively associated with the manipulator to cause the manipulator to perform movements in response to inputs on the hand control, the hand control being positioned relative to the image display device to permit an operator to manipulate the hand control while viewing responsive movements of the manipulator in the image displayed on the image display device; and
   a control system which determines the operative association between the hand control and the manipulator so as to cause the manipulator as viewed in the image displayed on the display device to appear as if it extends from the hand control so that in use, an operating environment is induced in which the viewed image of the manipulator and the hand control appear to be integral portions of a single hand-held instrument.

2. A telesurgical system as claimed in claim 1, which includes at least two remote controllable manipulators at the work station and at least two operatively associated hand controls at the operator station, each hand control being operatively associated with one of the manipulators to cause that manipulator to perform movements in response to inputs on its associated hand control, the control system determining the operative association between each hand control and its associated manipulator so as to cause the manipulators as viewed in the image displayed on the display device to appear as if they extend from the hand controls so that, in use, the viewed image of each manipulator and its associated hand control appears to be integral portions of a single hand-held instruments.

3. A telesurgical system as claimed in claim 2, wherein each hand control is mounted for movement about a pivot point and each manipulator is mounted for movement about a pivot point.

4. A telesurgical system as claimed in claim 2, wherein the endoscope is a stereo endoscope and the image display device is arranged to provide a corresponding stereo image.

5. A telesurgical system as claimed in claim 2, wherein the operative association between the hand control and the manipulator includes servo-control.

6. A telesurgical system as claimed in claim 3, which includes position sensors provided on the respective hand controls and manipulators, the position sensors being operatively connected in the control system to enable the control system to determine the positions of the hand controls and the manipulators, respectively, within at least one reference coordinate system.

7. A telesurgical system as claimed in claim 6, wherein the at least one reference coordinate system is a Cartesian reference coordinate system.

8. A telesurgical system as claimed in claim 2, which includes a magnification arrangement for magnifying the image captured by the endoscope.

9. A telesurgical system as claimed in claim 8, wherein the control system is arranged to cause the appearance that the displayed images of the manipulators appear to extend from their associated hand controls so that the operating environment in which the viewed image of each manipulator and its associated hand control appears to be integral portions of two separate hand-held instruments is again induced after the image is magnified.

10. A telesurgical system as claimed in claim 9, wherein the control system includes a processor arranged to compute a new position of each hand control relative to the image display device at which new positions the hand controls correspond to new positions of the manipulators as viewed in the magnified image displayed on the image display device.

11. A telesurgical system as claimed in claim 10, which includes a displacement arrangement for displacing the hand controls into their new positions.

12. A telesurgical system as claimed in claim 11, wherein the displacement arrangement is operatively connected in the control system to enable the control system to instruct the displacement arrangement to displace the hand controls into their new positions.

13. A telesurgical system as claimed in claim 12, wherein the control system is arranged to instruct the manipulators to be locked in their positions while the hand controls are caused to be displaced into their new positions.

14. A telesurgical system as claimed in claim 13, in which the processor computes offsets relating to the new positions of the hand controls relative to the positions of the manipulators and uses these offsets in determining the operative association between the hand controls and the manipulators thereafter.

15. A telesurgical system including
   a work station having an endoscope for capturing an image of a surgical site and at least two manipulators arranged to perform at least part of a surgical procedure at the surgical site, each manipulator movable about a pivot point;
   a remote operator station having an image display device operatively associated with the endoscope to display the image captured by the endoscope and at least two hand controls operatively associated with the manipulators, each hand control being mounted for movement about a pivot point and operatively associated with one of the manipulators to cause that manipulator to perform movements in response to inputs on its associated hand control, the hand control being positioned relative to the image display device to permit an operator to manipulate the hand control while viewing responsive movements of the manipulator in the image displayed on the image display device; and
   a control system which determines the operative association between each hand control and its associated manipulator so as to cause the manipulators as viewed in the image displayed on the display device to appear as if they extend from the hand controls so that, in use, an operating environment is induced in which the viewed image of each manipulator and its associated hand control appear to be integral portions of two integrally connected hand-held instruments, position sensors being provided on the respective hand controls and manipulators, the position sensors being operatively connected in the control system to enable the control system to determine the positions of the hand controls and the manipulators, respectively, within at least one reference coordinate system, wherein the endoscope is movably mounted at the work station to enable the endoscope to be moved from one position into a new position relative to the surgical site.

16. A telesurgical system as claimed in claim 15, wherein the control system is arranged to cause the appearance that the viewed image of each manipulator and its associated hand control appears to be integral portions of two separate integrally connected hand-held instruments to be reestablished after the endoscope is moved into a new position.

17. A telesurgical system as claimed in claim 16, wherein the control system and manipulator effect movement of the endoscope about a pivot point.

18. A telesurgical system as claimed in claim 16, wherein the control system is arranged to cause the endoscope to displace angularly about a viewing axis thereof in reestablishing the appearance that the displayed images of the manipulators appear to extend from their associated hand controls so that the operating environment in which the viewed image of each manipulator and its associated hand control appears to be integral portions of a single hand-held instruments is again induced.

19. A telesurgical system as claimed in claim 15, wherein position sensors are provided at appropriate positions relative to the endoscope, the position sensors being operatively connected in the control system to enable the control system to determine the position of the endoscope within at least one reference coordinate system.

20. A telesurgical system as claimed in claim 19, wherein the reference coordinate system is a Cartesian reference coordinate system.

21. A telesurgical system as claimed in claim 18, wherein the control system includes a processor arranged to compute a new position of each hand control relative to the image display device at which new positions the hand controls correspond to new positions of the manipulators as viewed in the image displayed on the image display device.

22. A telesurgical system as claimed in claim 21, which includes a displacement arrangement for displacing the hand controls into their new positions.

23. A telesurgical system as claimed in claim 22, wherein the displacement arrangement is operatively connected in the control system to enable the control system to instruct the displacement arrangement to displace the hand controls into their new positions.

24. A telesurgical system as claimed in claim 22, in which the displacement arrangement is arranged to provide tactile feedback during the performance of a surgical procedure.

25. A telesurgical system as claimed in claim 23, wherein the control system is arranged to instruct the manipulators to be locked in position while the hand controls are caused to be displaced into their new positions.

26. A telesurgical system as claimed in claim 25, wherein the processor computes offsets relating to the new positions of the hand controls relative to the positions of the manipulators and uses these offsets in determining the operative association between the hand controls and the manipulators thereafter.

27. A telesurgical method comprising:

positioning a surgical end effector within an internal surgical site in a patient body, the surgical end effector operatively associated with a hand controller via a processor so that the processor effects movement of the end effector in response to movement of the hand controller;

capturing an image of the surgical end effector within the internal surgical site with an endoscope;

displaying the image of the end effector so that the end effector defines a displayed position relative to the hand controller;

moving the endoscope within the internal surgical site;

statically realigning the displayed position of the image of the end effector relative to the hand controller so as to compensate for the endoscope moving step by transforming the displayed position of the image of the end effector so that the end effector is superimposed on the hand controller in the view of a surgeon operating the hand controller.

28. A telesurgical system including, a work station having an endoscope for capturing an image of a surgical site and at least one manipulator arranged to perform at least part of a surgical procedure at the surgical site;

a remote operator station having an image display device operatively associated with the endoscope to display the image captured by the endoscope and at least one hand control operatively associated with the manipulator to cause the manipulator to perform movements in response to inputs on the hand control, the hand control being positioned relative to the image display device to permit an operator to manipulate the hand control while viewing responsive movements of the manipulator in the image displayed on the image display device; and a control system which determines the operative association between the hand control and the manipulator so as to cause the manipulator as viewed in the image displayed on the display device to appear as if it extends from the hand control so that in use, an operating environment is induced in which the viewed image of the manipulator and the hand control appear to be integral portions of a single integrally connected hand-held instrument, the endoscope movably mounted at the work station to enable the endoscope to be moved from one position into a new position relative to the surgical site, the control system arranged to reestablish the integral instrument appearance of the manipulator and the hand control after the endoscope is moved into a new position.

* * * * *